United States Patent [19]

Rubinstein

[11] Patent Number: 4,498,960
[45] Date of Patent: Feb. 12, 1985

[54] ELECTROCHEMICAL METHOD FOR VISUAL DETECTION OF NONMETALLIC SURFACE INCLUSIONS IN METALLIC SUBSTRATES

[75] Inventor: Israel Rubinstein, Schenectady, N.Y.

[73] Assignee: General Electric Company, Schenectady, N.Y.

[21] Appl. No.: 438,116

[22] Filed: Nov. 1, 1982

[51] Int. Cl.³ .............................................. B01D 59/40
[52] U.S. Cl. ....................................................... 204/1 T
[58] Field of Search ............................ 204/1 T; 324/52

[56] References Cited

U.S. PATENT DOCUMENTS

| 3,123,806 | 3/1964 | Alburger | 204/1 T |
| 3,419,479 | 12/1968 | Klein | 204/1 T |
| 3,530,045 | 9/1970 | Alburger | 204/1 T |

OTHER PUBLICATIONS

Diaz et al., "Electrochemical Polymerization of Pyrrole", *Journal of the Chem. Soc. Chem. Communications* (1979), pp. 635–636.

Noufi et al., "Protection of Semiconductor Photoanodes with Photoelectrochemically Generated Polypyrrole Films", *J. Electrochemical Soc.*, vol. 128, No. 12, (1981), pp. 2596–2599.

Schoot et al., "New Electrochromic Memory Display", *Appl. Phys. Lett.*, vol. 23, No. 5, (Jul. 15, 1973), pp. 64–65.

Primary Examiner—John F. Niebling
Attorney, Agent, or Firm—Paul E. Rochford; James C. Davis, Jr.; James Magee, Jr.

[57] ABSTRACT

An electrochemical method for fast and non-destructive visual detection of nonmetallic surface inclusions in metallic substrates is provided. The method uses electrode modification techniques, wherein, for example, a monomer is electrochemically polymerized, to form a dark film on the metallic substrate, thus causing any nonconductive inclusions, which will not be coated with the film, to appear bright and highly visible.

11 Claims, 9 Drawing Figures

ELECTROCHEMICAL METHOD FOR VISUAL DETECTION OF NONMETALLIC SURFACE INCLUSIONS IN METALLIC SUBSTRATES

BACKGROUND OF THE INVENTION

Parts and components made of high-strength alloys for use in aircraft, space vehicles and power generation equipment generally are more susceptible to failure due to cracking than parts and components made from lower strength alloys. Those cracks typically propagate from defects such as nonmetallic inclusions resulting primarily from the alloy making processes and cracks resulting from component fabrication processes such as welding and grinding.

All steel and superalloy ingots contain to some degree nonmetallic matter, i.e., inclusions, consisting almost exclusively of oxides, with lesser amounts of sulphides, in various combinations and mixtures with each other. Such inclusions are derived chiefly from the oxidizing reactions of the refining process and the deoxidizing materials added to the alloy in the furnace, ladle, or molds. A few inclusions may also result from erosion of the refractories used to line the vessels used in alloy making processes.

Given that all metallic components can contain inclusions and cracks, there is a design trade-off between alloy strength and component weight which is influenced to no small degree by the ability to reliably and nondestructively detect defects as small as those which can cause failure.

For example, the life of gas turbine disks made from high-strength superalloys can be limited by low-cycle fatigue (LCF) endurance. First failures in LCF are typically initiated at surface, or near-surface, inclusions and features, e.g., carbides, as small as 5–100 square mils in size. Presently, the only method used for quality control is low-cycle fatigue tests on samples machined from disks. The LCF testing technique suffers from two major drawbacks, both related to its destructive nature: (1) it is expensive and (2) it cannot be applied to every single part produced. A more desirable approach would be a fast, nondestructive surface inclusion-related technique which could be used on the finished component or on sections of the billet from which the components are to be produced.

SUMMARY OF THE INVENTION

A nondestructive surface inclusion-related test for the visual detection of nonmetallic surface inclusions in metallic substrates is provided by the electrode modification methods of this invention. Briefly, and generally, the method of this invention comprises the steps of immersing the component or sample to be tested into an electrolytically conductive bath containing at least an active material and passing an electric current between the component or sample as a first electrode and a second electrode spaced apart from the first electrode thereby precipitating a continuous dark coating on the surface of the component or sample. Any nonconducting inclusions present will not be coated, but will be highlighted against the dark background.

One presently preferred active material is the polymerizable monomer pyrrole which when electrochemically oxidized to polypyrrole forms a dark film on the surface of the component or sample. Another useful active material is the heptyl viologen (II) ion in an aqueous solution containing a high concentration of bromide ions which when electrochemically reduced forms a dark-violet film of a water-insoluble monobromide salt on the surface of the part or component inspected.

The method of the invention is fast, reproducible, easy to use, can be used with different types of surface finishes and readily lends itself to automation using computerized optical detectors.

DESCRIPTION OF THE PREFERRED EMBODIMENTS

Figure 1A:
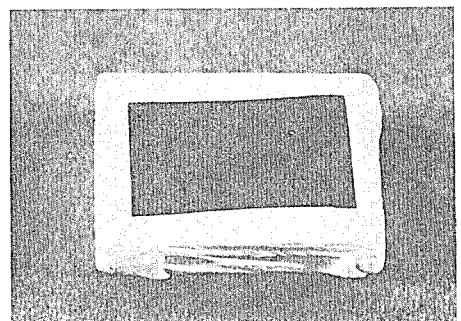
FIG. 1A is a 2× photomacrograph of the polished surface (Type A) of an Inconel-718 specimen without implanted oxide inclusions following nondestructive inspection by the method of the invention using a polymerizable monomer.

As set forth in the foregoing summary, the invention relates to a method for the rapid, nondestructive testing of metallic objects or substrates, e.g., finished components, parts or samples of the metal from which the parts or components were made or are to be made, for the presence of nonmetallic surface inclusions. Thus, the surface, or a representative preselected portion of the surface, of the object to be tested must first be suitably prepared. Generally, the smoother the surface, the smaller are the inclusions which can be detected. Typically, inclusions on the order of about 10 square mils can be detected by the method of the invention on a surface machine finished to about 32 root-mean-square (rms) smoothness.

Next, the object to be tested is cleaned. A procedure which has been found to be satisfactory is to rinse the object with acetone for approximately 10 minutes in an ultrasonic bath, repeat the rinsing a second time using isopropanol, repeat the rinsing a third time using distilled water and blow-drying the object using, e.g., a hot-air gun. Trichloroethylene may be used in place of the isopropanol in the first step if potential corrosion of the object from chlorinated hydrocarbons is of no concern.

The object to be tested is then immersed in an electrolytically conductive bath and the object is electrically connected to a direct current (DC) power source as a first electrode. A second electrode of a material inert in the bath, e.g., platinum or stainless steel, is connected to the DC power source and is also placed in the bath in a spaced apart (nontouching) relationship to the object to form an electrochemical cell. Preferably, the surface of the second electrode is shaped to conform to the shape of the object, or the particular surface of the object, to be tested. For example, a solid round object would preferably be placed inside a hollow cylinder for the placing of a solid round object spaced apart from a flat plate-like second electrode would result in a nonuniform electrochemical reaction. While reference is made to the immersion of the object into a bath, it should be recognized that the method of the invention is also workable with portable electrochemical cells and may, therefore, be used to test portions of components or parts in situ, e.g., in the field.

In one preferred embodiment, the electrolytically conductive bath will contain at least an active material in the form of a monomer which can be electrochemically polymerized and a solvent. If necessary, an inert salt may also be added to make the solution conductive. Preferably, the polymerized monomer is dark, e.g., deep blue or black, so that when it precipitates as a continuous coating on the surface of the object any nonconducting inclusions, which will not be coated, will appear as bright spots against a dark background.

The presently preferred monomer is pyrrole. Polymerization of pyrrole to polypyrrole occurs upon electrochemical oxidation of the monomer according to reaction (1):

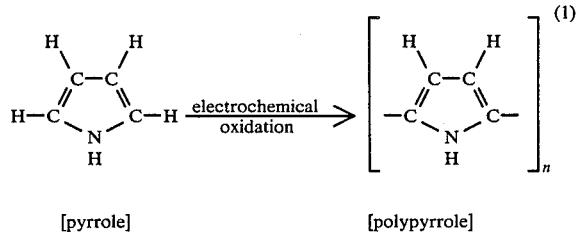

[pyrrole]   [polypyrrole]

to produce a black insoluble film on the object as the anode. A suitable bath contains 0.05–0.25M (molarity) distilled pyrrole as the active material plus 0.10–0.25M tetrabutylammonium fluoroborate (TBABF$_4$) as the supporting electrolyte in acetonitrile solvent. Electrochemical polymerization is accomplished at about 1.2 mA/cm$^2$ for about 2.5 to 3.5 minutes to form a coating about 0.5 microns thick. After completion of the electrochemical polymerization, the object is removed from the bath, rinsed with clean acetonitrile and then with distilled water, and then blow-dried. Observation and a permanent photographic record can be made on the dried object or the object can be observed in situ, i.e., under acetonitrile or water. Inclusions as small as about 5 mils$^2$ (~60$\mu$ dia.) can readily be observed with the unaided eye while magnifying means may be required to detect smaller inclusions. The coated samples can also be rinsed, dried and stored for archival purposes, if desired. The bath may be reused until it becomes brownish which is indicative of excessive pyrrole oxidation.

An alternate electrode modification technique of the invention is the electrochemical reduction of heptyl viologen (II) ion (HV$^{2+}$) as the active material in an aqeuous solution containing a high concentration of bromide ions to deposit a dark-violet film of the water-insoluble monobromide salt heptyl viologen (I) bromide (N,N'-diheptyl-4,4'-bipyridinium bromide, or HV+Br−) on the component or part according to reaction (2):

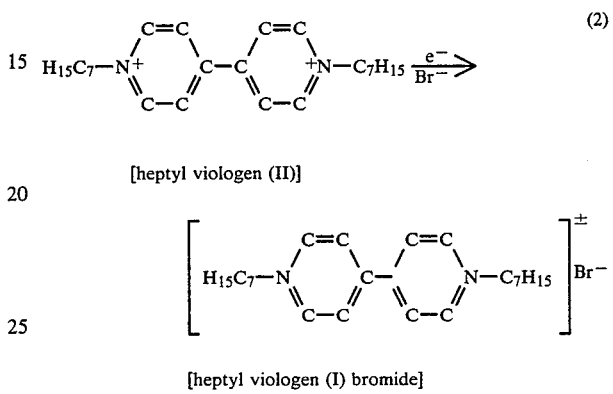

A suitable aqueous bath contains about 0.01M heptyl viologen (II) ion (HV$^{2+}$) and about 0.2M bromide salt, e.g., KBr. The electrochemical reduction is typically performed at a constant potential of about −0.65 volt [versus a saturated calomel electrode (SCE)] for about 10–30 seconds. The results must be observed in situ, i.e., in the bath, since exposure of the object to air causes fast oxidation of the film and disappearance of the dark-violet color. The layer of heptyl viologen (I) bromide can be easily removed by either electrochemical oxidation at more positive potentials or by exposing the substrate to air (oxidation with O$_2$) and rinsing with water.

The following examples are given by way of illustration, and not by way of limitation, of the novel method herein described for the rapid, nondestructive testing of metallic objects for the presence of nonmetallic surface inclusions.

EXAMPLE I

One surface each of several rectangular samples of Inconel*-718 a nickel-base superalloy, were prepared using two techniques. Highly polished (metallographically finished-Type A) surfaces were prepared by sequentially polishing with 1.0, 0.3, and 0.05$\mu$ alumina powder and less-highly-polished surfaces (about 16 rms-Type B) were prepared by polishing with 600-grit silicon carbide paper. The samples were wrapped with Teflon** tape to leave only the specially prepared Types A and B surfaces exposed.

*Inconel is a Registered Trademark of the International Nickel Co., Inc.
**Teflon is a Registered Trademark of E. I. DuPont de Nemours & Co.

"Artificial" oxide inclusions were implanted on the prepared surfaces of some of the Inconel-718 samples by sputtering Al$_2$O$_3$ through small holes in an aluminum mask placed over the sample surfaces. The hole diameters were such that deposits of about 280, 180, 120, 90, 60 and 30 microns in diameter were formed. The sputtered samples and some unsputtered control samples were subsequently cleaned using the cleaning procedure described above in detail.

The prepared and cleaned samples were immersed separately in an acetonitrile bath containing 0.25M distilled pyrrole plus 0.25M tetrabutylammonium fluoroborate (TBABF$_4$) with the exposed surface situated opposite to and spaced from an inert planar platinum foil electrode having about the same surface area as the exposed sample surface.

Application of a constant direct current to provide a current density of 1.2 mA/cm$^2$ for 2.5 to 3.5 min. with the sample as the anode resulted in the deposition of a continuous adherent black polypyrrole film on the samples. The nonconducting nonmetallic sputter-deposited inclusions were not coated; rather they were clearly visible with high resolution and contrast down to the smallest size against the black polypyrrole film.

Figure 1B:
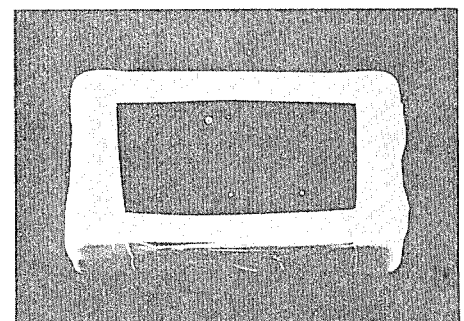
FIG. 1B is a 2× photomacrograph of the polished surface (Type A) of an Inconel-718 specimen having six sputter-deposited alumina inclusions thereon ranging in size from about 30 to 280 microns in diameter following nondestructive inspection by the method of the invention using a polymerizable monomer.
Figure 1C:
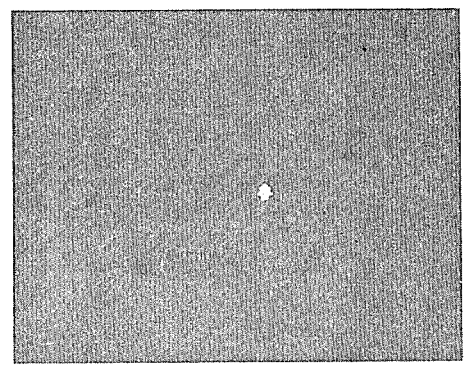
FIG. 1C is a 164× photomacrograph of the polished surface (Type B) of an Inconel-718 specimen showing a sputter-deposited alumina inclusion about 33 microns in diameter following nondestructive inspection by the method of the invention using a polymerizable monomer.

A representative sample with a Type A surface finish, but without sputter-deposited inclusions, is shown in FIG. 1A. A similar sample with a Type A surface finish and sputter-deposited oxide inclusions is shown in FIG. 1B; an inclusion having a diameter of about 280 microns ($\sim$95 mils$^2$) is located in the lower right hand corner and an inclusion having a diameter of about 30 microns ($\sim$1.1 mils$^2$) is shown in the upper left corner. The same results were obtained irrespective of whether the surface finish was Type A or B. A representative sample with a Type B surface finish (600 grit sand-paper) and an inclusion having a diameter of about 33 microns ($\sim$1.3 mil$^2$) is shown in FIG. 1C at 164×.

EXAMPLE II

Alumina (Al$_2$O$_3$) powder of known size range was mixed with powder having a composition corresponding to René-95, a nickel-base superalloy, to form alumina-doped specimens similar in shape to those of Example I, by powder metallurgy techniques. One surface each of several of the doped René-95 specimens were prepared to a Type B finish and several to a Type C (machine ground, approx. 32 rms) finish, cleaned, and nondestructively tested by the method of the invention set forth in Example I.

Figure 2A:
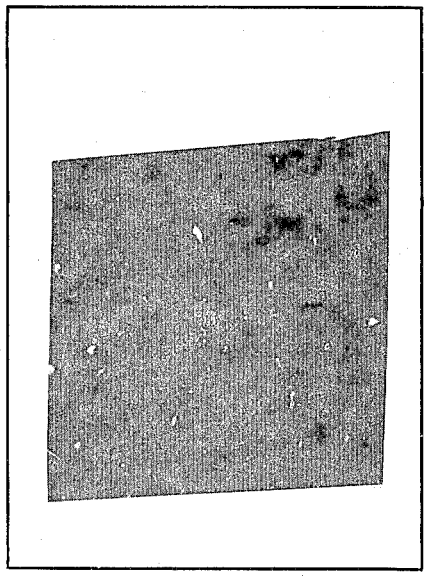
FIG. 2A is a 16× photomacrograph of the polished surface (Type B) of a René-95 specimen doped with alumina inclusions about 80 mils$^2$ following nondestructive testing by the method of the invention.
Figure 2B:
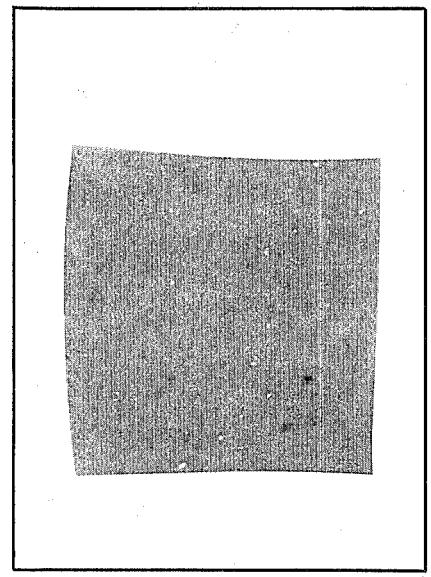
FIGS. 2B and 2C are similar to FIG. 2A except the inclusions are about 30 and 4 mils$^2$, respectively.
Figure 2C:
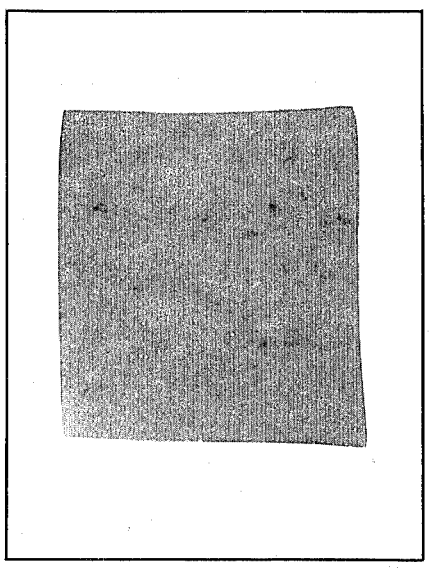
Figure 2D:
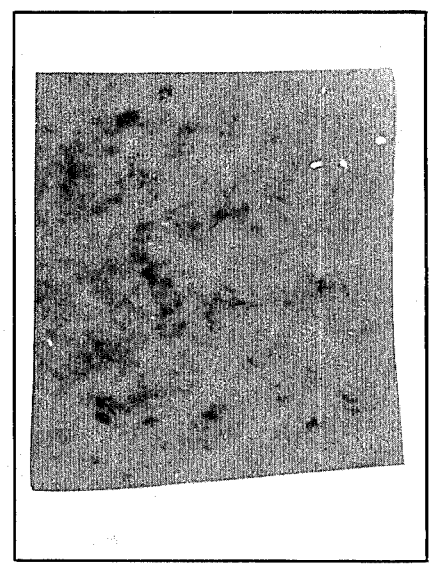
FIG. 2D is similar to FIG. 2A except the surface finish is Type C and the doped-in inclusions are about 30 mils$^2$.

FIGS. 2A, 2B and 2C show how readily doped-in surface inclusions about 80, 30 and 4 mils$^2$, respectively, are visually detected against the black polypyrrole film on Type B surfaces and FIG. 2D shows how readily doped-in surface inclusions about 30 mils$^2$ are similarly detected on Type C surfaces.

EXAMPLE III

A specimen of Inconel-718 of the type described in Example I having six sputter-deposited artificial inclusions of various sizes on a Type A surface was immersed in an aqueous solution of about 0.01M heptyl viologen (II) ion (HV$^{2+}$) and about 0.2M KBr opposite and spaced apart from an inert platinum foil electrode. This solution was conveniently prepared by dissolving 5.14 grams of N,N'-Diheptyl-4,4'-bipyridinium dibromide (C$_{24}$H$_{38}$Br$_2$N$_2$—MW=514.40) (0.01 mole) plus 23.8 gram KBr (0.2 mole) with enough water to make one liter. The HV$^{2+}$ ion need not necessarily be supplied as the dibromide salt as other salts capable of supplying the HV$^{2+}$ ion should be useable.

Figure 3A:
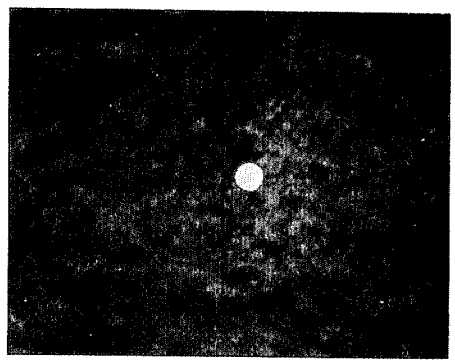
FIG. 3A is a 90× photomacrograph of the polished surface (Type A) of an Inconel-718 specimen showing a sputter-deposited alumina inclusion about 60μ in diameter following nondestructive testing by the method of the invention using heptyl viologen (II) ion as the active material.
Figure 3B:
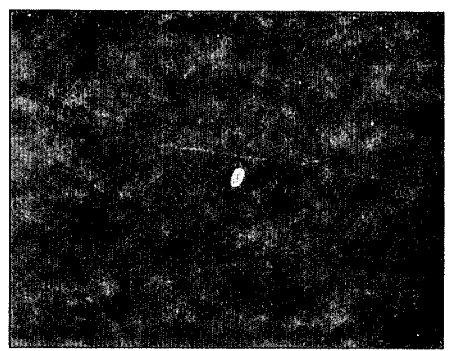
FIG. 3B is the same as FIG. 3A except the inclusion shown is about 3μ in diameter.

The specimen was cathodically polarized at $-0.65$ volt (versus SCE) for about 20 seconds. A continuous dark-purple layer of the water-insoluble salt heptyl viologen (I) bromide (HV$^+$Br$^-$) precipitated on the surface of the specimen causing the six nonconductive uncoated inclusions to appear as bright spots against the dark background. Two of the smaller inclusions thus revealed are shown in FIGS. 3A (8 mil$^2$) and 3B (1.7 mil$^2$) as photographed in situ.

It will be understood that various changes and modifications not specifically referred to herein may be made to the invention described without departing from the spirit of the invention particularly as defined in the following claims.

What is claimed is:

1. The method of preparing metallic objects for nondestructive inspection for the presence of nonmetallic surface inclusions comprising the steps of:
   (a) immersing the metallic object to be nondestructively tested into an electrolytically conductive bath containing at least an active monomer material, and
   (b) passing a direct electric current between said object as a first electrode and a second electrode of a material inert in said bath and spaced apart from said object for a time sufficient to polymerize said monomer and deposit on the conducting portions of the surface of said object a thin, dark, substantially continuous film of polymer formed from said monomer.

2. The method of claim 1 wherein said active material is pyrrole, said bath contains 0.05 to 0.25M pyrrole plus 0.10 to 0.25M tetrabutylammonium fluoroborate in acetonitrile, said electric current is about 1.2 mA/cm$^2$, and said time is about 2.5 to 3.5 minutes.

3. The method of claim 1 wherein said object is made of a nickel-base superalloy.

4. The method of claim 1 wherein the surface of said object to be inspected has a metallographically polished finish.

5. The method of claim 1 wherein the surface of said object to be inspected has a surface finish of about 16 to 32 rms.

6. The method of claim 1 wherein said second electrode has a surface area approximately equal to the area of the surface of said object to be inspected and is shaped to substantially conform to the contour of said surface to be inspected.

7. The method of preparing metallic objects for nondestructive inspection for the presence of nonmetallic surface inclusions comprising the steps of:
   (i) immersing the metallic object to be nondestructively tested into an electrolytically conductive bath, said bath containing 0.05 to 0.25M pyrrole plus 0.10 to 0.25M tetrabutylammonium fluoroborate in acetonitrile and
   (ii) passing a direct electric current at about 1.2 mA/cm$^2$ between said object as the anode and a cathode of a material inert in said bath and spaced apart from said object for about 2.5 to 3.5 minutes.

8. The method of claim 5 wherein said object is made of a nickel-base superalloy.

9. The method of claim 5 wherein the surface of said object to be inspected has a metallographically polished finish.

10. The method of claim 5 wherein the surface of said object to be inspected has a surface finish of about 16 to 32 rms.

11. The method of claim 5 wherein said second electrode has a surface area approximately equal to the area of the surface of said object to be inspected and is shaped to substantially conform to the contour of said surface to be inspected.

* * * * *